United States Patent [19]
Chanda et al.

[11] Patent Number: 5,645,587
[45] Date of Patent: Jul. 8, 1997

[54] PREVENTION OF CALCIFICATION AND DEGENERATION OF BIOLOGICAL TISSUE GRAFTS FOR IMPLANTATION IN HUMANS

[76] Inventors: Jyotirmay Chanda, Bejpara, Sreedhar Tank Road, Jessore 7400, Bangladesh; Ryosei Kuribayashi, 187- Higashida, Kashiwagimachi, Hiraka, Minami tsugaru-gun, Aomori 036-01, both of Japan

[21] Appl. No.: 658,694

[22] Filed: Jun. 5, 1996

[51] Int. Cl.$^6$ .................................................. A61F 2/10
[52] U.S. Cl. ........................ 623/11; 424/569; 424/572; 435/1.1; 435/374; 435/366; 435/371
[58] Field of Search .................................. 623/11

[56] References Cited

U.S. PATENT DOCUMENTS

| | | | |
|---|---|---|---|
| 5,104,787 | 4/1992 | Lindstrom et al. | 435/1 |
| 5,336,616 | 8/1994 | Livesey et al. | 435/240.2 |
| 5,383,927 | 1/1995 | De Goicoechea et al. | 623/1 |

*Primary Examiner*—John G. Weiss
*Assistant Examiner*—John M. Black
*Attorney, Agent, or Firm*—Delbert R. Phillips

[57] ABSTRACT

The present invention relates to chemical treatment for prevention of calcification and degeneration of biological tissue grafts used as a whole or in a part as heart valve substitutes, substitutes of blood vessel, pericardial substitutes, and surgical membranes for implantation in human. The process includes the steps of treatment of the grafts with partially degraded heparin to prevent the calcification of glutaraldehyde-treated xenografts.

11 Claims, No Drawings

PREVENTION OF CALCIFICATION AND DEGENERATION OF BIOLOGICAL TISSUE GRAFTS FOR IMPLANTATION IN HUMANS

BACKGROUND OF INVENTION

1. Field of Invention

The present invention relates to the biological prosthetic materials including heart valves, vessels, pericardium, dura mater, skin, amniotic membrane, umbilical cord, muscle tendons, ligaments, fascias and gut of mammalian origin used as a whole or in a part as grafts for various organs and tissues. This invention is particularly suitable for replacement or repair of heart valves, blood vessel, pericardial tissues and other body membranes.

2. Description of the Prior Art

Bodily tissue replacement surgery has been established over the past 30 years, particularly in the area of valve and organ replacement. The field has been shared between biological and mechanical replacement in the repair of tissues and organs. In the area of biological replacement of heart valves, glutaraldehyde treated porcine heart valves, have been used as an improvement over mechanical valves. Carpentier A et at., *J Torah Cardiovasc Surg* 58:467–82, (1969). Dystrophic calcification is chief cause of failure of bioprosthetic heart valves derived from glutaraldehyde-treated porcine aortic valves, Schoen F J et al. *Human Pathol;* 16:549–59(1985). Schoen F J et at. *Cardiovasc Clin;* 18:289–17 (1988). Ibrahim M et al. *J Thorac Cardiovasc Surg;* 108:221–30(1994).

Calcific deposits in either porcine valves or bovine pericardial valves are evident in residual connective cells of bioprosthetic tissue within 48 hours of subcutaneous implantation. Initial nucleation sites are located in cell membranes, cell nuclei, and intracellular organelles, such as mitochondria. Cell-associated deposits of calcium increase in size and number over time after implantation. These deposits obliterate cells, dissect among collagen bundles, and ultimately form gross nodules similar to those associated with clinical failures. Direct collagen involvement subsequently occurs. Schoen F J et al. In: Bodnar E, ed. *Surgery for heart valve disease: The proceedings of the 1989 symposium.* 679–85 (1990). The components of a valve can be divided into two parts with respect to their degree of antigenicity: (1) cells, water soluble proteins, mucopolysaccharides, and structural glycoproteins which had a high degree of antigenicity and. (2) collagen and elastin which appear to be less antigenic. In some instances, collagen can induce an immunological response. Carpentier A et al. *J Thorac Cardiovasc Surg,* 58:467–82(1969).

Concerning the prevention of calcification, various chemical techniques have been used but the results are inconclusive. Inhibition of mineralization of bioprosthetic valves implanted subcutaneously in small size animals has been achieved through pretreatment with various chemical components Carpentier A et al., *Circulation;* 70 (suppl 1): 165–8(1984). Lentz D J et al., *Trans Am Soc Artif Intern Organs,* 28:494–8 (1982) and with systemic or local controlled release of diphosphonate, Webb C L et al., *Ann Thorac Surg,* 46:309–16(1988). Levy R J et al., *Circulation* 71:349–56(1985). T6 (sodium dodecyl sulfate) processing inhibits the onset of intrinsic mineralization in glutaraldehyde-fixed xenograft tissue, Lentz D J et al. Cohn L W, Galluci V, eds. *Cardiac biotissue grafts. Proceedings of the Second International Symposium.* New York: Yorke Medical Books., 306–19(1982). T6 treatment did not significantly affect the onset and degree of bioprosthetic calcification, Thurbrikar M J et al., *Trans Am Soc Artif Intern Organs,* 29:245–9 (1983). Toluidine blue is the calcium retarding agent employed in the Medtronic-Intact porcine valve. Although the biochemical mechanism by which the toluidine blue process modifies the calcification is unknown. It is presumed that toluidine blue treatment inhibits or retards calcification of collagen, while the calcification of cellular components remains unaffected Valence M et al., Bodnar E, ed., *Surgery for heart valve disease: The proceedings of the 1989 symposium,* 668–76(1990). Preincubation in aluminum chloride ($AlCl_3$) significantly inhibits calcification of bovine pericardium in 60 days after being subcutaneously implanted in rats. Iron also inhibits calcification of bioprosthetic tissue Schoen F J et at., Bodnar E, ed. *Surgery for heart valve disease: The proceedings of the 1989 symposium.* London: ICR Publishers, 679–85(1990). Other methods to reduce calcification of biotissue grafts, such as acyl-azide treatment, Petite H et at., *J Biomed Mater Res.,* 24:179–87(1990) and dye mediated photo oxidization, Moore M A et al., *J Biomed Mater Res,* 28:611–8(1994) have been reported. It also has been reported that L-Glutamic acid posttreatment significantly reduces the calcification of glutaraldehyde treated bioprosthetic material subcutaneously implanted in rats Grabenvörger M et al. *J Biomed Mater Res,* 26:1231–40(1992). According to unpublished work by the inventors, it is not apparent that temperature has a positive effect on calcium mitigation of biotissue grafts, however it has been reported that pretreatment of porcine aortic valve in glutaraldehyde at high temperature (50° C.) alone mitigates calcification in both subcutaneous and circulatory models Carpentier S M et at., *Ann Thorac Surg,* 69:S332–8(1995). It has been reported that $\alpha$-amino oleic acid (AOA) posttreatment prevents calcification of glutaraldehyde treated bioprosthetic heart valves, Girardot M N et al., *Trans Soc Biomater.,* 14:114 (1991). In all valves implanted in mitral position in young sheep for 5 months, AOA-treated valves had morphologic features suggesting generalized tissue degradation, including structural loosening, surface roughening, and deep cuspal collections of erythrocytes, Gott J P et al., *Ann Thorac Surg,* 53:207–16(1992). Moreover, the treatment with $\alpha$-amino oleic acid did not prevent the calcification of aortic wall in sheep study Chen W et al., *Circulation* 90:323–9 (1994). Researchers have found that the tissue extraction process significantly reduces the propensity of xenograft calcification in vivo, Vesely I. et al., *Ann Thorac Surg,* 60:S359–64(1995). The extent of glutaraldehyde cross-linking is clearly important, although the specific mechanisms by which glutaraldehyde fixation facilitates mineralization are not understood Webb C L et at., *Ann Thorac Surg* ;46:309–16(1988). The slow release of residual (unbound) glutaraldehyde from the prosthesis over a period of time after implantation reinforces the host plasma calcium-acid bound complex. This acid-plasma calcium complex promotes further mineralization when glutaraldehyde plays no more role as the primary factor for nucleation of calcification. Chanda J., *Ann Thorac Surg,* 60:S339–42(1995)

In cells modified by aldehyde cross-linking or mechanical injury, cell membranes are disrupted (leading to increased permeability), and mechanisms for calcium extrusion are no longer fully functional. Moreover, high energy phosphates (particularly ATP) required to fuel these mechanisms are unavailable. Thus, calcium accumulation occurs unimpeded with a dramatic increase in intracellular calcium Schoen F J et al., *Cardiovasc Clin,;* 18/2:28917(1988); Webb C L, et al., *Ann Thorac Surg,* 46:309–16(1988). When glutaraldehyde treatment is used alone, elimination of highly antigenic substances such as cellular elements and water soluble proteins, does not prevent the calcification of glutaraldehyde-treated biotissue grafts implanted in adult rats. Moreover, further treatment with glutarahyde does not prevent calcification. Chanda J., *Ann Thorac Surg*, 60:S339–42(1995). Inactivation of residual glutaraldehyde and unbound aldehyde moieties on the surface of the tissue gratis, either with amino compound like chitosan (a biopolymer) or glycine+gentamicin completely prevents the calcification of glutaraldehyde-treated biotissue grafts implanted subdermally in adult rats (120–150 g), Chanda J., *Ann Thorac Surg* 60:S339–42; Chanda J., *Artif Organs*, 18:408–10(1994). However inactivation of free impaired aldehydes either with chitosan, or glycine+gentamicin, or chitosan in combination with glycine and gentamicin does not prevent the calcification of glutaraldehydetreated biotissue grafts when implanted subdermally in weanling (3-week-old, 30–50 g) rats.

Heparin has potent anti-growth effect in smooth muscle cells Hoover R L et al., *Circ Res*, 47:578–83(1980). It also has been shown that heparin binds to the surface of cells Hiebert L M et at., *Thromb Res*, 8:195–04(1976) Different reactions used to break down heparin are known Shively J et al., *Biochemistry*, 15:3932–42. (1976). Method for covalent binding of heparin to artificial surfaces has been developed, Larm O et at., *Biomat Med Dev Art Org*, 11:161–73(1983) At present heparin coated tube is widely used as cardiopulmonary bypass circuit in open heart surgery. Heparin as one of various forms of glycosaminoglycan may be used in preparation of artificial skin substitute (wound dressing) U.S. Pat. No. 5,489,304 to Orgill et al. issued Feb. 6, 1996.

SUMMARY OF THE INVENTION

The present invention, describes a biotissue grafts formed by covalently binding heparin to glutaraldehyde-treated xenografts or heterografts which are used in biological tissue grafts. These biological tissue grafts do not calcify nor are subject to thrombosis after implantation.

The xenografts or heterografts are prepared by treating the tissues removed from the animal with glutaraldehyde which covalently binds to the tissues. The glutaraldehyde treated tissues are reacted with amino compound (chitosan-glycine-gentamicin). The tissues grafts and then reached with partially degraded heparin which effectively prevents calcification after implantation of tissue grafts.

Coupling of partially degraded heparin completely prevents the calcification of glutaraldehydechitosan-treated porcine pulmonary valve, aortic valve or pericardium implanted in weanling rats for more than 5 months. Heparin bonding after neutralization of residual glutaraldehyde with amino compound like chitosan, glycine, gentamicin, is essential in prevention of calcification of glutaraldehyde treated tissue grafts. It is necessary that the concentration of glutaraldehyde for cross linking the tissue graft does not exceed 0.25%.

DETAILED DESCRIPTION OF THE PREFERRED EMBODIMENT

Calcification (accumulation of calcium salt) is the main cause of failure of bioprosthetic heart valves. This pathological process occurs much faster in children and young patients than that in older patients (more than 60 years of age ). The exact mechanism of this calcification process is unknown. At present all commercially available heterograft heart valve substitutes are made of glutaraldehyde-treated porcine aortic valves or bovine pericardium. Highly antigenic substances like easily-extractable water soluble proteins and cellular elements of grafts can be removed by treatment with hypertonic solution and proteolytic enzyme like trypsin, and this can be started immediately after harvesting the grafting materials. To make the graft nonantigenic (inert), and to stabilize collagen material glutaraldehyde cross-linking is necessary. At 37° C. glutaraldehyde cross-links with collagen fibers of grafts much faster. Stabilization process of collagen fibers with glutaraldehyde is completed within one month if the concentrations of glutaraldehyde is gradually increased from 0.1% to 0.25%. No special buffer is necessary for the preparation of glutaraldehyde solution. Normal saline is sufficient for required dilution. Posttreatment with amino compounds prevents the slow-release of residual glutaraldehyde, and inactivates the free aldehyde moieties on the surface of the glutaraldehyde-treated tissue grafts. Chitosan, gentamicin, glycine serve these purposes. Due to the presence of large number of amino termini, one chitosan [$\alpha$(I-4)amino-2deoxy-$\beta$-D-glucan] (mol. wt. 2200–86000) molecule covalently cross-links with free aldehyde moieties on the surface of the glutaraldehyde-treated biotissue grafts and simultaneously inter-links other chitosan molecules with the help of residual glutaraldehyde which is slowly released from the treated tissue. As chitosan alone can not react with all aldehyde groups of glutaraldehyde, addition of glycine-gentamicin mixture neutralizes all remaining free aldehyde moieties. Despite complete inactivation of aldehyde moieties, chitosan-glycine-gentamicin post treated glutaraldehyde-treated biotissue grafts, do calcify after implantation subdermally in 3-week-old rats and in systemic circulation in juvenile sheep. To block the potential binding sites, modify charges and fill intertropocollagen spaces, heparin is necessary. Free aldehyde moieties of partially degraded heparin bind covalently with the free amino groups of chitosan and gentamicin. Further free aldehyde groups of already coupled heparin are blocked by cross-linking with chitosan-glycine-gentamicin. Compounds containing aldehyde (CHO—) functions react with primary amines to yield relatively labile Schiff bases that can be converted to stable secondary amines by reduction with sodium borohydride. These biotissue grafts can easily be stored in normal saline containing glycine and gentamicin. In vivo studies showed that bioprosthetic material prepared according to the above described method did not calcify when compared with only glutaraldehyde-treated materials and can be used in replacement therapy and grafting in mammals including humans.

EXAMPLE

Porcine aortic and pulmonary valves, and pericardium were washed in 5% sodium chloride for 24 hours at 4° C. These materials were rinsed in copious mounts of deionized water, and incubated in trypsin (Trypsin 1:250, Difco Labs, Detroit, Mich., USA) in normal saline (pH 7.4) for 40 minutes at 37° C. Then, all grafts were cross-linked in glutaraldehyde in normal saline (pH 7.4) with gradually increasing concentrations of glutaraldehyde (Glutaraldehyde EM 25%, TAAB Laboratories Equipment Ltd., Reading, UK) from 0.1 to 0.25% at 37° C. for a period of one month. Glutaraldehyde-treated grafts were placed first in 0.1% chitosan (Sigma Chemical Co., St. Louis, Mo., USA) solution for two weeks, then in a solution of 0.05% chitosan, 1% glycine (Glycine, Sigma) and 0.015% gentamicin sulfate (Schering-Plough, Osaka, Japan) for two weeks, and finally in 1% glycine-0.015% gentamicin sulfate solution for a week. Heparin (Heparin sodium salt 164.5

I.U./mg, Nacalai Tesque Inc., Kyoto, Japan) was partially degraded by nitrous acid generated in situ by addition of sodium nitrite (Wako Pure Chemical Industries Ltd. Tokyo, Japan) and hydrochloric acid (Nacalai) to the heparin solution (pH 2.0) at 4° C. for a period of 3 hours. On completion of the partial degradation, the pH of the solution was adjusted to 7.4 with 1N sodium hydroxide (Nacalai). All previously treated materials were cross-linked in a solution containing 0.1% partially degraded heparin for a week. Heparin bonded grafts were thoroughly washed in normal saline and kept in a solution of 0.05% chitosan, 1% glycine and 0.015% gentamicin sulfate for an additional week. Sodium borohydride (Wako) was dissolved in deionized water containing 1N sodium hydroxide (1 ml/1 liter $H_2O$) to titrate the pH up to 8.4. Treated grafts were placed in 0.06% sodium borohydride solution for 24 hours at room temperature, followed by washing in normal saline and 0.1% chitosan solution for 10 minutes. Then all specimens were kept in a solution containing 0.05% chitosan, 1% glycine and 0.015% gentamicin sulfate for 3 days and were stored in normal saline containing 0.5% glycine and 0.03% gentamicin sulfate until they were implanted.

Although this invention has been described and illustrated by reference to certain specific examples, these are exemplary only and the invention is limited only in scope by the following claims and functional equivalents thereof.

What is claimed as new and desired to be protected by Letters Patent is set forth in the appended claims.

We claim:

1. A calcification retardant bioprosthetic xenograft comprising removing tissue from a donor animal; cross-linking said tissue with glutaraldehyde;

treating said cross-linked tissue with partially degraded heparin; and treating said cross-linked tissue with gentamicin, glycine and chitosan before treatment with degraded heparin.

2. The xenograft as claimed in claim 1 wherein said cross linked tissue is treated with said partially degraded heparin for a period of one week.

3. The xenograft as claimed in claim 1 wherein said tissue is selected from the group consisting of heart valves, vessels, pericardium, dura mater, skin, amniotic membrane, umbilical cord, muscle tendons, ligaments, fascias and gut.

4. A method for treating a xenograft tissue to prevent in vivo calcification and degeneration comprising;

cross-linking tissue with glutaraldehyde; treating said cross-linked tissue with partially degraded heparin in normal saline;

said cross-linked tissue is treated with a solution containing chitosan, glycine and gentamicin sulfate in normal saline solution before binding with partially degraded heparin.

5. The method of claim 4 wherein a concentration of partially degraded heparin in the normal saline used for binding is 0.1 weight percent.

6. The method of claim 4 wherein said cross-linked tissue is treated with said partially degraded heparin for a period of one week.

7. The method of claim 6 wherein said cross-linked tissue is treated with said partially degraded heparin for three consecutive one week periods.

8. The method of claim 7 wherein said treated tissue is stored in normal saline containing glycine and gentamicin.

9. The method of claim 7 wherein after a final heparin binding said cross-linked tissue is washed first in chitosan then in chitosan-glycine-gentamicin sulfate in normal saline.

10. The method of claim 4 wherein said xenograft tissue is primarily cross-linked in glutaraldehyde in normal saline (pH 7.4) not more than 0.25 weight percent.

11. The method of claim 4 wherein said xenograft tissue is selected from the group consisting of heart valves, vessels, pericardium, dura mater, skin, amniotic membrane, umbilical cord, muscle tendons, ligaments, fascias and gut of mammalian origin.

* * * * *